United States Patent [19]
Schmitt

[11] Patent Number: 5,487,858
[45] Date of Patent: Jan. 30, 1996

[54] PROCESS OF MAKING SELF-SUPPORTING WOVEN VASCULAR GRAFT

[75] Inventor: Peter J. Schmitt, Garnerville, N.Y.

[73] Assignee: Meadox Medicals, Inc., Oakland, N.J.

[21] Appl. No.: 189,305

[22] Filed: Jan. 31, 1994

Related U.S. Application Data

[62] Division of Ser. No. 49,230, Apr. 19, 1993, Pat. No. 5,282,848, which is a continuation of Ser. No. 573,932, Aug. 28, 1990, abandoned.

[51] Int. Cl.⁶ .......................... B29C 67/00; B29D 23/00
[52] U.S. Cl. .......................... 264/103; 264/233; 264/234; 264/294
[58] Field of Search .................................. 264/103, 233, 264/234, 235, 294, 342 R, 342 RE, 344, 345, 346

[56] References Cited

U.S. PATENT DOCUMENTS

| | | |
|---|---|---|
| 2,836,181 | 5/1958 | Tapp . |
| 3,096,560 | 7/1963 | Liebig et al. . |
| 3,272,204 | 9/1966 | Artandi et al. . |
| 3,304,557 | 2/1967 | Polansky . |
| 3,316,610 | 5/1967 | Manock . |
| 3,479,245 | 11/1969 | Manock . |
| 3,479,670 | 11/1969 | Medell . |
| 3,853,462 | 12/1974 | Smith . |
| 3,878,565 | 4/1975 | Sauvage . |
| 3,945,052 | 3/1976 | Liebig . |
| 3,953,566 | 4/1976 | Gore . |
| 3,986,828 | 10/1976 | Hoffman, Jr. et al. . |
| 4,047,252 | 9/1977 | Liebig et al. . |
| 4,187,390 | 2/1980 | Gore . |
| 4,191,218 | 3/1980 | Clark . |
| 4,192,020 | 3/1980 | Davis . |
| 4,306,318 | 12/1981 | Mano et al. . |
| 4,340,091 | 7/1982 | Skelton . |
| 4,517,687 | 5/1985 | Liebig et al. . |
| 4,530,113 | 7/1985 | Matterson . |
| 4,632,842 | 12/1986 | Karwoski et al. . |
| 4,652,263 | 3/1987 | Herweck et al. . |
| 4,652,264 | 3/1987 | Dumican ................... 623/1 |
| 4,718,907 | 1/1988 | Karwoski et al. . |
| 4,892,539 | 1/1990 | Koch ........................... 623/1 |
| 4,987,665 | 1/1991 | Dumican et al. ........... 28/218 |

FOREIGN PATENT DOCUMENTS

| | | |
|---|---|---|
| 122744 | 10/1984 | European Pat. Off. . |
| 820014 | 9/1959 | United Kingdom . |
| 8303752 | 11/1983 | WIPO . |
| 8705796 | 10/1987 | WIPO . |
| 8905371 | 6/1989 | WIPO . |

*Primary Examiner*—Leo B. Tentoni
*Attorney, Agent, or Firm*—Hoffmann & Baron

[57] ABSTRACT

A woven synthetic fabric tubular vascular graft including, a stiffening component in the filling yarn is self supporting without crimping the walls of the graft. The graft is woven from warp ends of multifilament polyester yarns and elastomeric yarns in the warp and a filling yarn which includes multifilament and monofilament polyester yarns which have been twisted together. Longitudinal and radial compliance provide for improved kink resistance making the tubular grafts suitable for use in medium and small diameter peripheral applications. A preferred graft has an outer velour surface and a smooth inner surface.

9 Claims, 1 Drawing Sheet

PROCESS OF MAKING SELF-SUPPORTING WOVEN VASCULAR GRAFT

This is a divisional application of application Ser. No. 08/049,230, filed Apr. 19, 1993, now U.S. Pat. No. 5,282, 848, which is a continuation of application Ser. No. 07/573, 932, filed Aug. 28, 1990, now abandoned.

BACKGROUND OF THE INVENTION

This invention relates to synthetic vascular grafts, and more particularly to synthetic woven vascular grafts including a stiffening component to provide a non-crimped self-supporting graft.

Vascular grafts of synthetic materials are widely used for the replacement of segments of human blood vessels. Synthetic vascular grafts have taken a wide variety of configurations and are formed of a wide variety of materials. Among the accepted and successful vascular graft implants are those formed from a biologically compatible material in tubular form which retain an open lumen to permit blood to flow normally through the graft after implantation. The biologically compatible materials include thermoplastic materials such as polyester, polytetrafluoroethylene (PTFE), silicone and polyurethanes. The most widely used are polyester fibers and PTFE. The polyester fibers, usually Dacron, may be knit or woven and may be of a monofilament, multifilament or staple yarn, or combination of each.

There are a wide variety of synthetic vascular grafts presently in use. An important factor in the selection of a particular graft is the porosity of the substrate of which the graft is formed, the resiliency of the tubular construction and the strength requirements for the implant. Porosity is significant, because it controls the tendency to hemorrhage during and after implantation and influences ingrowth of tissue into the wall of the graft.

Synthetic fabric vascular grafts may be of a woven, knitted with or without a velour construction. A synthetic vascular graft having a warp-knit construction is disclosed by William J. Liebig in U.S. Pat. No. 3,945,052. Another graft having a warp knit double-velour construction is described by Liebig and German Rodriquez in U.S. Pat. No. 4,047,252. William J. Liebig and Dennis Cummings describe a synthetic woven double-velour graft in U.S. Pat. No. 4,517,687; the velour loops being formed of warp yarns which are preshrunk texturized multifilament yarns. These three issued United States patents for synthetic vascular grafts are assigned to the assignee of this application.

U.S. Pat. No. 4,892,539 issued to Durmus Koch describes a synthetic fabric woven graft with a single velour on the outer surface. The graft is described as woven from multifilament polyester yarns, specifically described as texturized, with the single outer velour formed of filling yarns with each velour loop extending outside a plurality of warp yarns.

After knitting or weaving multifilament yarns into tubular forms, the grafts are compacted by a method such as disclosed in U.S. Pat. Nos. 3,853,462 to Ray E. Smith and No. 3,986,828 to Harmon Hoffman and Jacob Tolsma also assigned to the same assignee as this application. Compaction results in shrinking of the yarns and generally reduces the overall porosity of the fabric substrate. These tubular grafts after compacting generally have a diameter from about 6 mm to 40 mm.

Subsequent to compacting, synthetic tubular fabric grafts are crimped. Crimping involves forming ridges in the wall of the grafts to eliminate the danger of kinking or collapse of the tubing when flexed and results in uniform, regular, circular corrugations which maintains uniform strength over the entire surface of the graft tubing. This applies to both the woven and knit fabric vascular grafts. Examples are shown by L. R. Sauvage in U.S. Pat. No. 3,878,565 who describes a tubular textile synthetic fiber prosthesis of a body having a multiplicity of outwardly extending fiber loops. In FIG. 2a, the graft body is crimped into irregular, circumferential corrugations. The degree of protection afforded by irregular corrugation varies over the lengths of the tube and can fall below the required level of protection at specific regions. The warp-knit and woven grafts described above in U.S. Pat. Nos. 3,945,052, No. 4,047,252 and 4,517,687 are circularly crimped graft in U.S. Pat. No. 4,892,539 is crimped in a spiral fashion. Crimped or corrugated walls can disrupt blood flow and create areas of thick tissue buildup, due to the profile.

S. Polansky in U.S. Pat. No. 3,304,557 avoids crimping in vascular prothesis by forming a tube with repeating reinforcing ring sections. These reinforcing ring sections incorporate reinforcing picks adjacent only the outer surface. He proposes that the annular rings can be in the form of a helix, alternating rings and helix-loops. These latter suggestions are similar to the tubular prosthesis of I. B. Medell in U.S. Pat. No. 3,479,670 wherein an open mesh tube is wrapped with two polypropylene monofilament right-hand and left-hand helices and fused to penetrate partially the exterior of the tube. In U.S. Pat. No. 3,272,204 to C. Artandi and L. D. Bechtol sew a Dacron fabric to Teflon rings or a helix to prevent an absorbable collagen reinforced graft tube from collapsing.

Selection of a particular type of graft substrate by a vascular surgeon depends upon several factors. Among the factors included is the particular location of the implantation. This also dictates the size of the graft in order to maintain a sufficiently large or small lumen to accommodate normal blood flow in the region of implantation. The ultimate strength requirements and blood pressure in the location of implantation also affect the selection. Generally, the woven grafts provide greater strength and reduced porosity, but are generally considered to be more difficult to handle and suture. Velours are often preferred because the velour surfaces facilitate growth of tissue into the loops extending from the surface of the velour fabric. The knitted grafts are generally softer and more easily sutured, but are generally more porous. Depending on the location of the implant and heparinization condition of the patient, synthetic fabric grafts generally must be preclotted with the patients blood before implantation. Preclotting may not be essential with a woven graft, but is generally recommended nonetheless.

Tubular grafts of smaller diameter, for example, 6 mm and below are often utilized in peripheral regions of the body and appendages. Today, the most successful in this respect are grafts of PTFE of the material disclosed by Robert W. Gore in U.S. Pat. Nos. 4,187,390 and No. 3,953,566. These grafts are formed by extrusion of the PTFE material. While accepted for use in small diameter applications, PTFE grafts often require surgical replacement within relatively short periods of time compared to the larger diameter fabric vascular grafts described above.

Accordingly, it is desirable to provide a synthetic fabric vascular graft suitable for a wide variety of dimensions and diameters providing the benefits of woven grafts, but which do not require crimping and will be self supporting and maintain an open lumen.

SUMMARY OF THE INVENTION

Generally speaking, in accordance with the invention, self-supporting woven synthetic vascular grafts having improved kink resistance including a stiffening component in the filling yarn is provided. The stiffening component of the filling yarns provides radial burst strength, dimensional stability and radial rigidity with resiliency to maintain the lumen of the tubular structure open and provide the necessary burst strength properties. The graft may also include low modulus elastomeric warp yarns. In one preferred embodiment, a plurality of elastomeric and multifilament warp yarns are woven in tubular form with a filling yarn of stiffer monofilament and multifilament yarn which have been twisted together. The elastomeric warp yarns provide longitudinal compliance (stretch) which aid in bending flexibility. The graft surfaces may be smooth or as a single or as a double velour.

In a single velour self-supporting vascular graft, the inner surface is provided with a fine, low profile woven surface to promote smooth, thin pseudointima formation. The loops on the exterior surface are formed multifilament warp yarns which provide the necessary texture cover for tissue adhesion and ingrowth. The multifilament warp yarns and the multifilament component of the filling yarns control blood porosity. The filling yarn is a monofilament yarn twisted with a multifilament yarn to provide required strength and reduce porosity.

The self-supporting woven grafts prepared in accordance with the invention are particularly well suited to 2–6 mm diameter peripheral vascular prosthesis, but are suitable for larger dimensions up to about 40 mm as well. Kink resistance is provided without the necessity to crimp the vascular graft.

Accordingly, it is an object of the invention to provide an improved woven synthetic vascular graft.

Another object of the invention is to provide a self-supporting woven synthetic vascular graft which resists kinking without the need to crimp the graft.

A further object of the invention is to provide a woven synthetic fabric vascular graft which is suitable for peripheral use in small diameters of 6 mm or less.

Still another object of the invention is to provide a small diameter woven synthetic fabric vascular graft which resists kinking and provides a desirable amount of longitudinal stretch without crimping.

Still a further object of the invention is to provide a self-supporting woven synthetic fabric vascular graft which includes an outer velour surface to promote tissue ingrowth.

Yet another object of the invention is to provide a self-supporting woven synthetic vascular graft having a fine, low profile woven surface to promote smooth, thin pseudointima formation.

Yet a further object of the invention is to provide a self-supporting woven synthetic fabric single-velour vascular graft having improved kink resistance without crimping.

Another object of the invention is to provide a method of preparing an improved self-supporting woven synthetic fabric vascular graft in accordance with the invention.

Still other objects and advantages of the invention will in part be obvious and will in part be apparent from the specification.

The invention accordingly comprises the several steps and the relation of one or more of such steps with respect to each of the others, the apparatus embodying features of construction, combination and arrangement of parts which are adapted to effect such steps, and the product which possesses the characteristics, properties, and relation of constituents (components), all as exemplified in the detailed disclosure hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
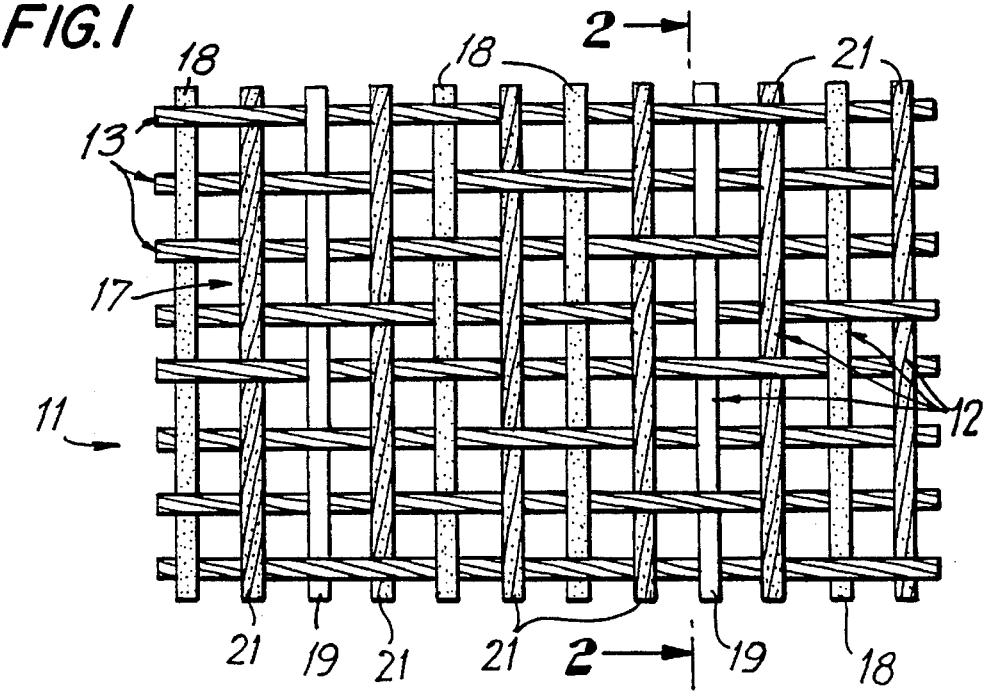
FIG. 1 is a weaving diagram of a woven synthetic fabric vascular graft prepared in accordance with a preferred embodiment of the invention.

The woven synthetic vascular grafts prepared in accordance with the invention are applicable to a wide range of diameters, including the small 2 to 6 mm diameter range suitable for peripheral use as well as dimensions up to about 40 mm. Accordingly, the grafts woven having inside diameters which range from about 2 to about 40 mm and are self-supporting and resist kinking without being crimped.

The stiffening component in the filling yarns may be a textile material, such as a monofilament yarn. Selection will vary depending on the desired characteristic of the tubular graft. However, the stiffening component must be sufficiently stiff to impart dimensional stability and radial rigidity to the tube without crimping. The stiffening component should have the following minimum physical properties:

Tenacity: $\geq 3$ grams per denier (53,000 psi)

Initial Modulus: $\geq 50$ grams/denier (800,000 psi)

EI: $\geq 3.9 \times 10^{-8}$ in$^2$.

Where EI is the bending stiffness, E is the initial modulus of elasticity, I is and moment of inertia. The diameter can vary depending on desired characteristics, but will typically be in the range of about 2 to 10 mils.

In one preferred embodiment of the invention, the woven graft has a diameter less than about 6 mm. In another preferred embodiment the woven graft has an exterior surface with loops and a smooth interior surface. The grafts are self-supporting and resistant to kinking without crimping the fabric surface. The grafts possess longitudinal elasticity imparted by including a plurality of thermoplastic low modulus elastomeric yarns as a component of the warp yarns. Elastomeric Yarns have properties which exhibit high stretch, low modulus, and good elastic recovery. Typical properties for yarns suitable for use would be:

Elongation to Break: >100%

Modulus of Elasticity: <1 gram per denier

Elastic Recovery: >80% or

Tensile Set: <20%

The resin can either be thermoplastic or thermoset, but should possess good biocompatibility. The remaining yarns utilized are those which are compatible biologically. Such yarns include polyethylene terephthalate, polyurethane, polytetrafluoroethylene and silicone.

Preferably, the majority of the yarn utilized in the woven graft is polyethylene terephthalate, such as DACRON available from du Pont. The remaining component is the elastomeric yarn which may be present in amounts ranging from about 2 to 20 percent by weight. The graft substrate is formed by weaving a plurality of warp yarns including elastomeric yarn and multifilament yarn with filling yarns of stiffer monofilament yarn and multifilament yarn which have been twisted together prior to weaving. The stiffer monofilament component of the filling yarn provides mechanical strength, dimensional stability and radial rigidity with resiliency which maintains an open lumen for normal blood flow and provides the necessary burst strength. The elastomeric warp yarn component provides longitudinal compliance which aids in bending flexibility.

The monofilament polyester utilized as a stiffening component in the Examples which follow is a 5 mil polyethylene terephthalate yarn. The yarn has the following physical properties:

Diameter: 0.005 inch (5 mils or 0.127 mm)

Tenacity: 6.2 grams per denier (110,000 psi)

Initial Modulus: 112 grams per denier (1,980,000 psi)

$$I \text{ (moment of inertia)} = \frac{\pi r^4}{64}$$

Calculated Bending Stiffness=E×I

EI=3.8×10$^6$ lb.in$^2$.

The multifilament warp yarns and multifilament component of the filling yarns provide the necessary texture and cover for tissue adhesion ingrowth on the outer surface and assist in controlling porosity of the graft. The velour loops are of multifilament warp yarns on the outer surface only. The inner surface has a fine, low profile which promotes smooth, thin pseudointima formation.

The particular selection of elastomeric and multifilament warp yarns together with the stiffer combined monofilament and multifilament filling yarns provide a graft having improved kink resistance over a wide range of diameters. Thus, smaller bending radii can be achieved without occluding. In the preferred single velour construction, the external velour surface promotes tissue ingrowth.

Figure 2:
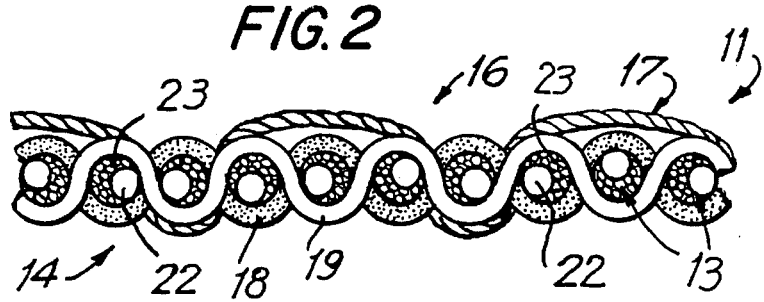
FIG. 2 is a cross-sectional view in schematic in the warp direction of a finished graft section showing the interlacing ends of filling yarn of a graft fabric of FIG. 1.

FIG. 1 illustrates the weaving pattern of a woven vascular graft substrate 11 prepared in accordance with a preferred embodiment of the invention. Substrate 11 is woven from a plurality of warp ends 12 and filling yarn 13. FIG. 2 is a schematic illustration of substrate 11 in cross-section with a smooth interior surface 14 and a velour exterior surface 16 having loops 17 of warp multifilament yarns 19 which stand away from the surface of the graft.

Referring to FIG. 1, warp yarns 12 include alternating ground warp ends of a first multifilament yarn 18, and a low modulus elastomeric monofilament yarn 19. In the illustrated embodiment multifilament yarn 18 is a one ply seventy denier preshrunk untexturized (flat) polyethylene terephthalate (DACRON) yarn (1/70/54) with a 5z twist. Elastomeric yarn 19 is a 140 Denier polyurethane (LYCRA Spandex) or an S-E-B-S (styrene-ethylene-butylene-styrene block copolymer). Two ends of multifilament ground warp yarn 18 alternate with one end of ground warp elastomeric yarn 19. The loop or pile component 19 of warp yarns 12 is a multifilament warp yarn 21 which alternates with each end of warp ground yarns 18 and 19. In substrate 11, multifilament yarn 21 is an untexturized unshrunk 2/40/27 with a 1.5s twist polyethylene terephthalate (Dacron) yarn.

Filling yarn 13 is a combined yarn of a monofilament yarn component 22 twisted together with a multifilament yarn component 23 to form filling yarn 13. In substrate 11, monofilament yarn 12 is a 5 mil polyethylene terephthalate monofilament yarn twisted with multifilament yarn component 23 which is a untexturized preshrunk yarn 2/40/27 (1.5s). This is the same yarn as untexturized preshrunk warp yarn 21. The components are twisted 1.5 turns per inch. in the s" direction.

Elastomeric component 19 of warp yarns 12 may be formed of any one of the biologically compatible materials having a low modulus of elasticity as noted above. The modulus of elasticity is typically less than 1 gram per denier with an elongation to break greater than 100 percent. For example, the elastic component may be a polyester, polyurethane, silicone or other compatible copolymers such as a styrene-ethylene-butylene-styrene block copolymer known as a C-Flex resin available from Concept Polymers. The elastomeric component is present in substrate 11 in an amount between about 2–20 percent by weight. Preferably, elastomeric component 19 is present in an amount about 5 to 10 percent by weight. The styrene-ethylene-butylene-styrene block copolymer monofilament yarn is 5 mil C-Flex. An alternative preferred yarn suitable for elastomeric component 19 is a Lycra polyurethane yarn of 140 denier.

Figure 3:
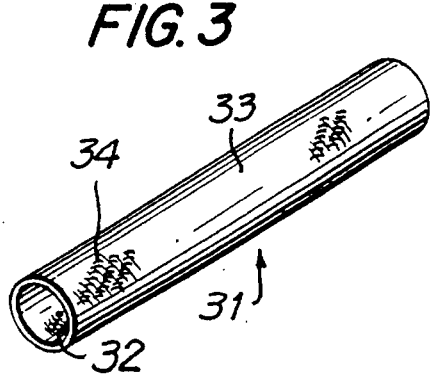
FIG. 3 is a perspective view having the weave pattern of a tubular woven single-velour vascular graft prepared in accordance with the invention.
Figure 4:
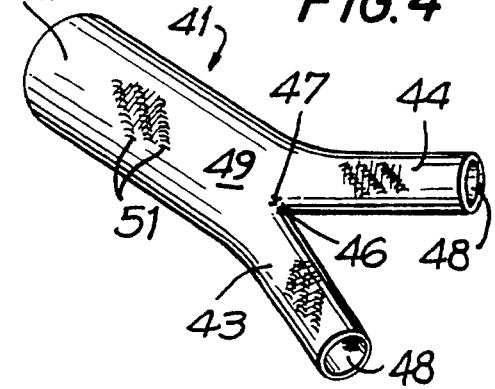
FIG. 4 is a perspective view of a bifurcated woven single-velour vascular graft prepared in accordance with the invention.

FIG. 3 is a perspective view of a tubular graft 31 prepared in accordance with the invention. Graft 31 has a smooth inner surface 32 and external velour surface 33 having a multiplicity of outwardly extending loops 34. Similarly, FIG. 4 illustrates a bifurcated graft 41 having a main body segment 42 and two legs 43 and 44. Legs 43 and 44 are joined to main body 42 at a crotch 46 which is generally reinforced by a row of stitches 47 to maintain as tight an initial porosity of the graft as possible. Graft 41 has a smooth interior surface 48 and an external surface 49 having loops 51.

As is evident from the weaving pattern of FIG. 1, loops 34 and 51 of grafts 31 and 41, respectively are formed from multifilament warp pile yarns. In substrate 11 the pile yarns are untexturized unshrunk polyester yarns 21.

After weaving substrate 11 in the pattern as shown in FIG. 1, grafts 31 and 41 are scoured and washed in a hot water and detergent bath which results in about 10 to 30 percent longitudinal shrinkage. The washed tubes are cut to desired lengths and heat-set in a convection oven on straight aluminum mandrels at about 175° C. for about 15 minutes to one hour. The grafts can also be heat set in a non-straight condition to create shaped grafts, such as an aortic arch, which will not have to be bent or shaped by the surgeon during implantation.

As discussed above, and as shown in FIGS. 3 and 4, tubular woven vascular grafts 31 and 41 prepared in accordance with the invention are not crimped in order to maintain an open lumen. This is due to inclusion of the relatively stiffer monofilament component 22 in filling yarns 13 and elastomeric component 19 in warp yarns 12.

The specifications of the yarn utilized and substrate 11 are set forth in the following Examples. These Examples are presented for purposes of illustration and are not intended in a limiting sense.

EXAMPLE 1

Tubular grafts were woven with the following yarns on the pattern of FIG. 1.

TUBULAR WEAVE CONSTRUCTION:
  Ground-weave for lattice structure: plain
  Warp float weave for loop or pile surface: crowfoot (floats on outside surfaces, See FIG. 2) alternates every other end (See FIG. 1)

YARN CONSTRUCTION:
  Warp Ground: 1/70/54 (5z) Untexturized Preshrunk
    DACRON 56 Polyester & 5 mil C-Flex, alternating 2
    ends of DACRON 56 Polyester and 1 end of C-Flex.
  Warp Float: 2/40/27 Texturized Unshrunk DACRON
    56 Polyester (1.5s).
  Filling: 5 mil PET Monofilament wound together with
    2/40/27 Texturized Preshrunk DACRON (1.5s).
  WEAVING DENSITY 320 ends per inch (40 dents/
    inch×8 ends/dent)
  Picks 60 picks per inch per layer (120 total) inserted.
TUBE DIMENSION:
  Greige Inside Diameters: 4.5, 5.5, 6.5 mm
  Finished Inside Diameters: 4, 5 & 6 mm.

EXAMPLE 2

In another preferred embodiment in accordance with the invention a 140 Denier LYCRA Spandex monofilament yarn is utilized as the elastomeric component 19 in the same pattern as substrate 11. Tubular vascular grafts having an identical weaving pattern as shown in FIG. 1 are formed with the following specifications:

TUBULAR WEAVE CONSTRUCTION
  Ground-weave for lattice structure: plain Warp float
    weave for loop or pile surface: (floats on outside
    surface, See FIG. 2) alternate on every other end
    (See FIG. 1);
YARN CONSTRUCTION:
  Warp Ground: 1/70/54 (5z) untexturized unshrunk
    DACRON 56 polyester and 140 Denier Lycra
    monofilament, alternating 2 ends of polyester and 1
    end of Lycra.
  Warp float: 2/40/27 (1.5s)-DACRON 56 Texturized
    Preshrunk polyester
  Filling: 5 mil PET Monofilament wound together with
    2/40/27 WEAVING DENSITY: preshrunk
    DACRON texturized 56 polyester.
  Sely: 320 epi (40 dents/inch×8 ends/dent)
  Picks: 60 picks per inch inserted per layer in tubular
    form.
TUBE DIMENSION:
  Greige Inside Diameters: 8 mm
  Finished Inside Diameter: 4.8 mm The velour for both grafts was formed by weaving every other end in a crowfoot pattern, which allows the warp yarn to float over three picks and under one pick. The remaining adjacent ends form a lattice structure. Every third ground end in the weaving plan is LYCRA or C-Flex, which in total means that one in six warp ends is elastomeric yarn. The elastomeric yarn causes the fabric to retract in length which raises the floats of the warp weaving in a crowfoot pattern to form loops.

After weaving, the self-supporting woven single velour graft material of Example 2 was scoured and dried and then rinsed to remove trace chemicals and dried again. Scouring shrank or relaxed the graft tubing about 20.5%. The relaxation which occurs contributes to the ultimate longitudinal stretch.

The tubing was pressed along the tubing edges to remove the crease line formed during weaving. The tubing was then cut to 36 cm lengths and heatset by sliding them onto straight aluminum mandrels at the cut length and placed into a convection oven at 121° C. for 20 minutes.

The Dimensional changes before and after finishing were as follows:

| Property | Example 2 |
| --- | --- |
| Longitudinal Shrinkage from greige to scoured, % | 20.5 |
| Longitudinal Shrinkage from scoured to heatset, % | 11.3 |
| Total longitudinal shrinkage from greige to heatset, % | 29.5 |
| Fabric count after weaving, epi × ppi | 192 ± 0 × 70.5 ± 2.2 |
| Fabric count after scouring, epi × ppi | 192 ± 0 × 88.1 ± 1 |
| Fabric count after heat setting, epi × ppi | 192 ± 0 × 100 ± 1 |

The porosity of the grafts was measured using a Wesolowski permeability tester. Six specimens were tested at two locations. The paired values were added together and reported as a single value. The grafts were tested both relaxed and stretched using a 4 lb weight. The results were as follows:

| | Permeability (ml/min/cm$^2$) | |
| --- | --- | --- |
| Graft | Relaxed | Stretched |
| WSV (Lycra) | 1004 ± 96 | 1284 ± 124 |

The average burst strength of the graft was determined by measuring six graft samples on an Instron Tensile Tester and was 509±58 psi.

A woven single velour graft woven with-LYCRA Spandex [WSV (LYCRA)] was tested for the force required to pull a suture from the end of the graft. One 2-0 Dexon suture was inserted through the graft 3 mm from the edge. The graft was mounted in the bottom pneumatic grip of the Instron Tensile Tester and the suture in the top grip. The tensile tester was activated to cause the suture to be torn from the graft. The graft exhibited a suture pullout of 7.50±.3 kg for a cut edge and 7.66±.21 kg for cauterized specimens.

Observations of the failed specimens disclosed that the cut edge grafts had an elongated hole before the filling yarns ruptured. The cauterized grafts had a more circular hole before rupture. This suggests that cauterizing the graft end is preferable to minimize distortion of the suture hole as well as prevent unravelling of the yarns during handling.

Thickness

The graft wall thickness and pile height was determined using SEM analysis. The average overall wall thickness was 0.80 mm with a pile height of 0.48 mm.

Longitudinal Compliance

The longitudinal compliance is a relative measurement of the ability of the graft to elongate at a given force and is expressed as the percent elongation per kilogram force. The longitudinal compliance was measured on an Instron Tensile Tester using pneumatic grips as follows.

The Instron was set to the following settings:

Full Scale Load: 2 kg

Crosshead Speed: 10 in/min

Chart Speed: 10 in/min

Gauge Length: 3 in

Load Cycling Limits: 0.1 kg to 1.0 kg

The specimens were mounted in the grips with a preload tension of 0.04 kg. The specimens were cycled between 0.1 and 1.0 kg for a total of 50 cycles. On the 50th cycle, the strip chart recorder was activated to record the event. After the last cycle, the crosshead was returned to the 0.1 kg force and stopped. The extension indicated on the digital readout was recorded. This value was added to the original gauge length of 3 inches to arrive at the effective gauge length for calculating the percent elongation and compliance. The average longitudinal compliance was 23.4%/kg.

Kink Resistance

The relative kink resistance was measured in a dry, non-pressurized condition. This was a quick test to see if the graft could be bent longitudinally without kinking. If or when it did kink, to what extent, as determined by the inside radius of curvature.

Four graft specimens, 15 to 20 cm in length, were looped in a circular fashion such that the ends were facing in opposite directions. The ends were slowly and gently pulled so as to reduce the diameter of the loop. The ends were pulled until the first evidence of kinking occurred in the wall of the grafts. This procedure took place on the surface of a metric ruler so that the inside diameter could be continuously monitored to capture the point of kinking.

The WSV (LYCRA) grafts kinked at a diameter of 18±1.7 mm. If we divide the diameter by two to obtain the inside radius of curvature and then divide this by the inside graft diameter of 4.8 mm, we obtain a 1.9±.2 Rad./Graft Diameter value which can be used for comparing to other grafts.

These grafts prepared in accordance with the invention are considered kink resistant, since they are flexible longitudinally and can be looped or bent to a significant degree. Typically, rigid or non-longitudinally compliant grafts or tubular structures will kink immediately upon the application of sufficient stress to deform the structure about their longitudinal axis.

Radial Compression

Radial compression of the graft was measured to determine the crush resistance of the graft. Four specimens between 15 and 20 cm in length were individually mounted into an Instron Tensile Tester with a flat plate compression apparatus, which measured 4 inches in diameter. The specimens were mounted into the compression apparatus so that the ends of the grafts extended beyond the ends of the plates. The gap between the upper and lower plates was reduced so that they came into contact with the specimens and exerted a preloaded force of 0.02 kg. The distance between the plates was measured with a Vernier to the nearest 0.5 mm, which is the initial gap. The crosshead travel was started at a rate of 0.5 inches/min and stopped when the grafts were completely compressed.

The strip charts generated were analyzed by measuring the slope of the curves to determine the compression moduli. The compression modulus is calculated by the following formula:

$$\text{Compression Modulus, g/cm} = \frac{\text{Force, g} \times \text{Initial gap, mm}}{\text{Displacement, mm} \times 4 \text{ in} \times 2.54 \text{ cm/in}}$$

In order to compare the values of two types of grafts with different diameters the modulus values can be normalized by multiplying them by the inside diameters of the graft. The resulting units are grams—millimeter diameter per centimeter length.

The self-supporting WSV (LYCRA) grafts exhibited a radial compression of 2850±182 g-mm/cm. The radial compression is an important property in contributing to the ability of a graft to resist kinking when deformed. If the radial compression is high with respect to longitudinal compliance or stiffness, then kink resistance is achieved. If radial compression is low, the wall of the graft is more flexible and consequently kinks more readily.

Graft substrate 11 in FIG. 1 includes every third ground warp end of elastomeric component 19 resulting in one in six warp ends being elastomeric component 19. Elastomeric component 19 causes substrate 11 to retract in length which raises the floats of the warp yarns in a crowfoot pattern to form loops 17. Filling yarn 13 includes texturized preshrunk polyester, but may be either texturized or untexturized depending on the shrinkage characteristics desired. The only requirement is that these yarns be multifilament to assist in reducing porosity of the graft and facilitating tissue adhesion ingrowth and after implantation. The stiff monofilament component of filling yarn 13 provides radial burst strength, dimensional stability and radial rigidity with resiliency to maintain an open lumen for normal blood flow and provide the necessary burst strength of the graft.

The characteristics and properties of the graft woven in accordance with the invention can be varied as desired by selection and combination of the starting warp and filling yarns and the weaving pattern. In the illustrated examples, the warp ground yarns are multifilament (or flat) polyester, but could be texturized or untexturized, or preshrunk or unshrunk, and elastomeric yarns. The preferred loop yarn is a multifilament texturized polyester yarn, but could also be untexturized preshrunk or unshrunk. The sole limiting feature is that there be sufficient multifilament yarns considering the desired end results. The filling yarn is a composite monofilament twisted with a multifilament component of texturized preshrunk yarn, which can also be untexturized or unshrunk.

It will thus be seen that the objects set forth above among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A process for preparing a self-supporting woven vascular graft, comprising:

weaving a plurality of warp yarns with a filling yarn including a stiffening component to provide a woven tubular fabric;

scouring said woven tubular fabric; and heat setting said woven tubular fabric to set said stiffening component in a generally rounded configuration thereby providing radial rigidity with resiliency to said woven tubular fabric without crimping resulting in a self-supporting woven vascular graft.

2. The process of claim 1, including weaving the tubular fabric with warp yarns of elastomeric yarn.

3. The process of claim 1, including weaving the tubular fabric with the stiffening component including a monofilament yarn.

4. The process of claim 1, wherein heat setting is carried out by placing the tubular fabric on a straight mandrel and heating to set the tubular fabric.

5. The process of claim 1, wherein heat setting is carried out by placing the tubular fabric on a curved mandrel and applying heat to set the tubular fabric.

6. The process of claim 1, including weaving the tubular fabric with warp yarns including multifilament yarns.

7. The process of claim 1, including weaving the tubular fabric with the filling yarn including multifilament yarns.

8. The process of claim 1, including weaving the tubular fabric into a bifurcated tube having a main body portion and two branches connected to the main body portion.

9. The process of claim 1, including weaving the tubular fabric with warp yarns including elastomeric yarn.

* * * * *

UNITED STATES PATENT AND TRADEMARK OFFICE
CERTIFICATE OF CORRECTION

PATENT NO. : 5,487,858
DATED : January 30, 1996
INVENTOR(S) : Schmitt

It is certified that error appears in the above-indentified patent and that said Letters Patent is hereby corrected as shown below:

At Col. 2, line 14,     "crimped graft in U.S. Pat. No. 4,892,539" should be -- crimped graft. The graft in U.S. Pat. No. 4,892,539--;

At Col. 3, line 3,     "the filling yarns provides" should be --the filling yarn provides--;

At Col. 4, line 42,     "EI: $\geq 3.9 \times 10^{-8} in^2$." should be --EI: $\geq 3.9 \times 10^{-8} lb.\text{-}in^2$--;

At Col. 4, line 44,     "of elasticity, I is and moment of inertia" should be --of elasticity and I is the moment--;

UNITED STATES PATENT AND TRADEMARK OFFICE
CERTIFICATE OF CORRECTION

PATENT NO. : 5,487,858

DATED : January 30, 1996

INVENTOR(S) : Schmitt

It is certified that error appears in the above-indentified patent and that said Letters Patent is hereby corrected as shown below:

At Col. 7, lines 9-10,     "WEAVING DENSITY 320 ends per inch (40 dents/inchx8 ends/dent) should be --WEAVING DENSITY--;

At Col. 7, after line 10,     Please insert --Sley 320 ends per inch (40 dents/inchx8 ends/dent)--;

At Col. 7, lines 36-37,     "2/40/27 WEAVING DENSITY: preshrunk DACRON texturized 56 polyester." should be --2/40/27 texturized preshrunk DACRON 56 polyester.--;

At Col. 7, after line 37,     please insert --WEAVING DENSITY:--;

UNITED STATES PATENT AND TRADEMARK OFFICE
CERTIFICATE OF CORRECTION

PATENT NO. : 5,487,858

DATED : January 30, 1996

INVENTOR(S) : Schmitt

It is certified that error appears in the above-indentified patent and that said Letters Patent is hereby corrected as shown below:

At. Col. 7, line 38,   "Sely: 320 epi (40 dents/inchx8 ends/dent)" should be --Sley: 320 epi (40 dents/inchx8 ends/dent)--;

At Col. 7, line 42,   "Greige Inside Diameters" should be --Greige Flat Width--;

At Col. 8, line 10,   "192 ± 0 x 88.1 ± 1" should be --192 ± 0 x 88.7 ± 1--

Column 10, line 9, "ingrowth and" should be --and ingrowth--

Signed and Sealed this

Twenty-fifth Day of June, 1996

Attest:

BRUCE LEHMAN

Attesting Officer   Commissioner of Patents and Trademarks